United States Patent [19]

Hudson

[11] Patent Number: 5,545,199
[45] Date of Patent: Aug. 13, 1996

[54] HOT AND COLD THERAPEUTIC PILLOW

[76] Inventor: Gary C. Hudson, 4601 Sulgrave Rd., Richmond, Va. 23220

[21] Appl. No.: 497,876

[22] Filed: Jul. 3, 1995

[51] Int. Cl.⁶ ............................................. A61F 7/00
[52] U.S. Cl. .................... 607/109; 607/114; 5/644
[58] Field of Search .................. 607/96, 98, 99, 607/109, 110, 114; 5/630–639, 644–646

[56] References Cited

U.S. PATENT DOCUMENTS 4,832,007  5/1989  Davis, Jr. et al. ........................... 5/644
4,858,259  8/1989  Simmons et al. ........................ 607/114
4,887,326  12/1989  O'Brien et al. .......................... 607/114
5,344,437  9/1994  Pistay ...................................... 607/114

Primary Examiner—Lee S. Cohen
Assistant Examiner—Herman J. Robinson
Attorney, Agent, or Firm—Kenway & Crowley

[57] ABSTRACT

A hot and cold therapeutic pillow which includes a cervical roll having relatively firm ends and a relatively soft middle portion. The core of the pillow is hollow and accommodates a cylindrical gel pack which may be heated by microwave radiation or cooled by freezing. The cervical roll may be integrally combined with a head cradle which has a soft middle or central portion and firm ends.

7 Claims, 3 Drawing Sheets

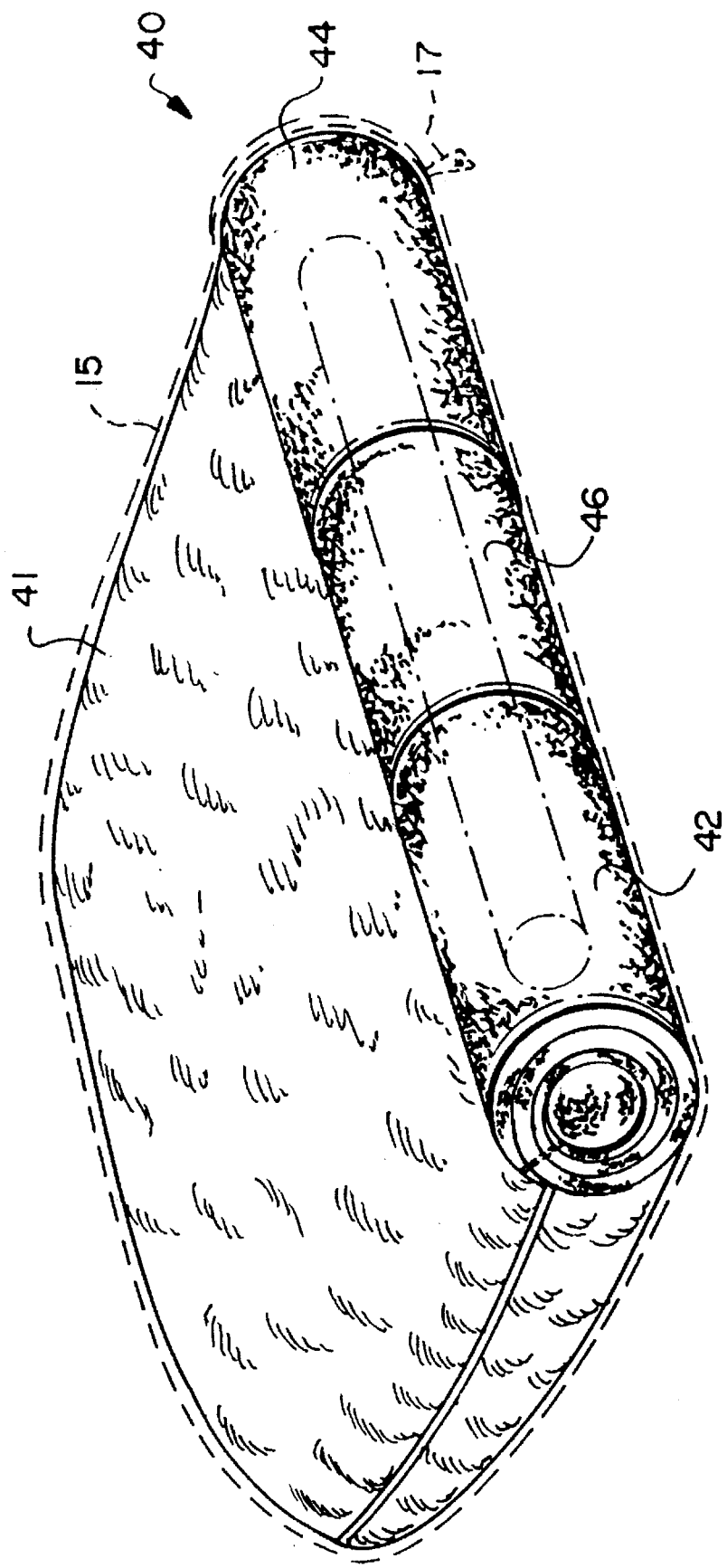

HOT AND COLD THERAPEUTIC PILLOW

This invention relates in general to pillows and in particular to a cervical roll pillow operable in hot or cold modes.

BACKGROUND OF THE INVENTION

The basic bed pillow is a simple support for the head and neck of a reclining person. Depending upon the user's preference, pillows have been made of any of a variety of materials, such as feathers, sponge rubber, and a number of plastics in the form of foam or batting. More recently, pillows have been contoured to give the user separate support of the neck and head, as well as to comfortably cradle the head for reading or television viewing while seated in bed. A currently offered refinement involves a pillow which, by the use of contoured plastic foam having convoluted surfaces, positions the head for comfortable sleeping posture and easier breathing.

There has also been some recognition that therapeutic functions can be performed by properly designed pillow structures, and this has led to the use of hot and cold packs which may be retained in pockets formed in the pillows. The available products of this type, however, are generally ill-designed to permit their effective use, particularly in neck and back areas. Also, the known products generally have a relatively low degree of comfort because of a lack of appropriate cervical support for the user.

A principal object of the present invention is to expand and improve the therapeutic functions of pillows.

Another object of the present invention is to retain and enhance the comfort derived from head and cervical roll pillows by providing cold or hot therapy to the neck, head or back.

A further object of the invention is the provision of a pillow which combines a head cradle with a cervical roll containing a therapeutic gel pack.

A still further object of the present invention is to improve the effectiveness, durability, and ease of cleaning of pillows having therapeutic gel packs.

SUMMARY OF THE INVENTION

The foregoing and other objects, features and advantages have been achieved basically by utilizing a novel cervical roll made of plastic such as polyurethane foam or polyester fiber. The roll has relatively firm end portions and a relatively soft central portion. It also has a hollow core and it is covered by a casing made from a layer of cotton and polyester fabric. At least one end opening is formed in the casing, and it is provided with a zipper closure. In the hollow core of the cervical roll of the pillow, there may be inserted a cylindrical gel pack for heating or cooling. The gel pack is removable to permit its being heated by microwave or cooled in a freezer. Also, of course, removal of the gel pack facilitates laundering of the pillow. There may be combined with the cervical roll a head cradle also made either from polyurethane foam or silicone slickened polyester fiber and having matching relatively firm end portions and a relatively soft central portion.

For a better understanding of the present invention, together with other objects, features and advantages, reference should be made to the following description of a preferred embodiment of the invention, which should be read with due consideration of the accompanying drawing in which like reference characters designate like parts, and in which:

BRIEF DESCRIPTION OF DRAWING

FIG. 3 is a perspective view of a combined cervical roll and head cradle pillow formed from polyester fiber batting.

DESCRIPTION OF PREFERRED EMBODIMENT

Figure 1:
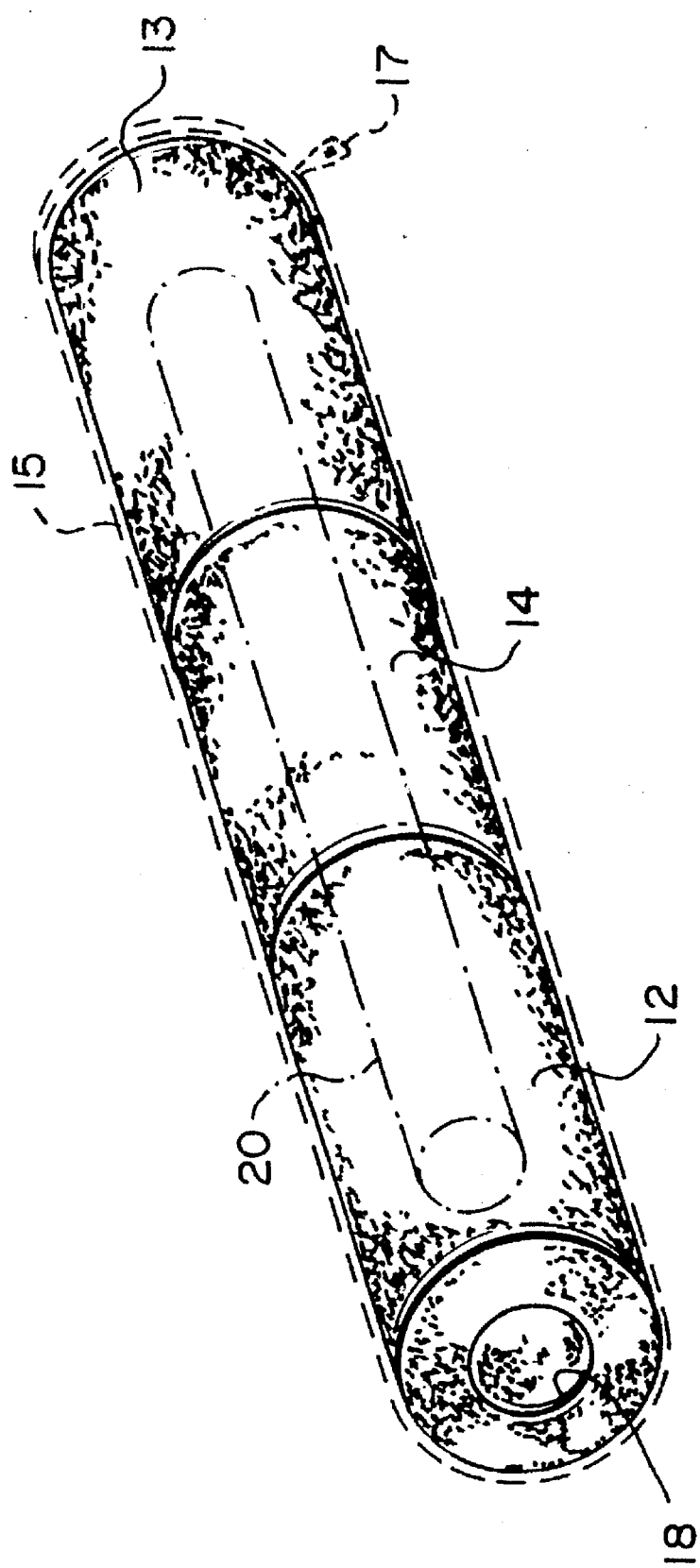
FIG. 1 is a perspective view of a therapeutic cylindrical cervical roll pillow.

In the perspective view of FIG. 1, a cervical roll is shown. The roll is cylindrical in cross-section and may be of a diameter of about 5". The roll is of laminated construction, having end portions 12 and 13 approximately 8" wide and made of relatively firm plastic material, and a central portion 14 approximately 6" wide of relatively soft plastic material. In the embodiment of the roll utilizing polyurethane foam, the end portions 12 and 13 are of polyurethane foam having a density of 1–1.8 lbs. per cubic foot and a firmness of 20 lbs. Indent Load Deflection. The central portion 14 also has a density of 1.0–1.8 lbs. per cubic foot, but has a firmness of 12 lbs. Indent Load Deflection.

The use of relatively soft foam in the central portion and relatively firm foam in the end portions permits the pillow to be bent in a curve and fitted about the neck. A central core opening 18 is formed throughout the length of the roll to permit the insertion of a cylindrical gel pack 20. The gel pack 20 is composed of a bladder which may be fabricated from 16-gage polyvinyl chloride material sealed by radio frequency to form a cylinder of about 2" in diameter and 17" in length. The bladder is filled with a fine organic powder of starch-grafted sodium polyacrylate, to which water has been added to form a sludge completely filling the bladder. The gel pack may be heated by microwave radiation in order to use the pillow for heat therapy. It also may be placed in a freezer to permit its use in cold therapy. Generally speaking, the gel pack may be subjected to microwave radiation for 2–2.5 minutes for hot therapy, and for cold therapy, the gel pack should be placed in a freezer for about 2 hours.

The roll may be covered with a casing of polycotton indicated in phantom at 15, and zippered openings indicated in phantom at 17 may be provided in one or both ends of the polycotton cover to permit the insertion and removal of the gel pack.

The roll may be provided with an adjustable strap connected to its ends in order that it may be curved to serve as a neck wrap fitted around and secured to the neck for hot or cold neck therapy. Of course, the pillow may also be used for hot and cold back therapy with or without the aid of the adjustable strap.

Although the preferred material for the roll is polyurethane foam as described above, other plastics such as polyester fiber may be used. When utilizing such a fiber, the filling in each of the 8-inch ends compared to the quantity of similar filling used in the 6-inch central portion. The polyester fiber may be silicone-slickened and in the form of batting which is basically twice as thick in the end portions of the cervical roll as compared to the central portion. Suitable polyester fiber material is 1 ¼" staples of 6 denier layered with resin.

Figure 2:
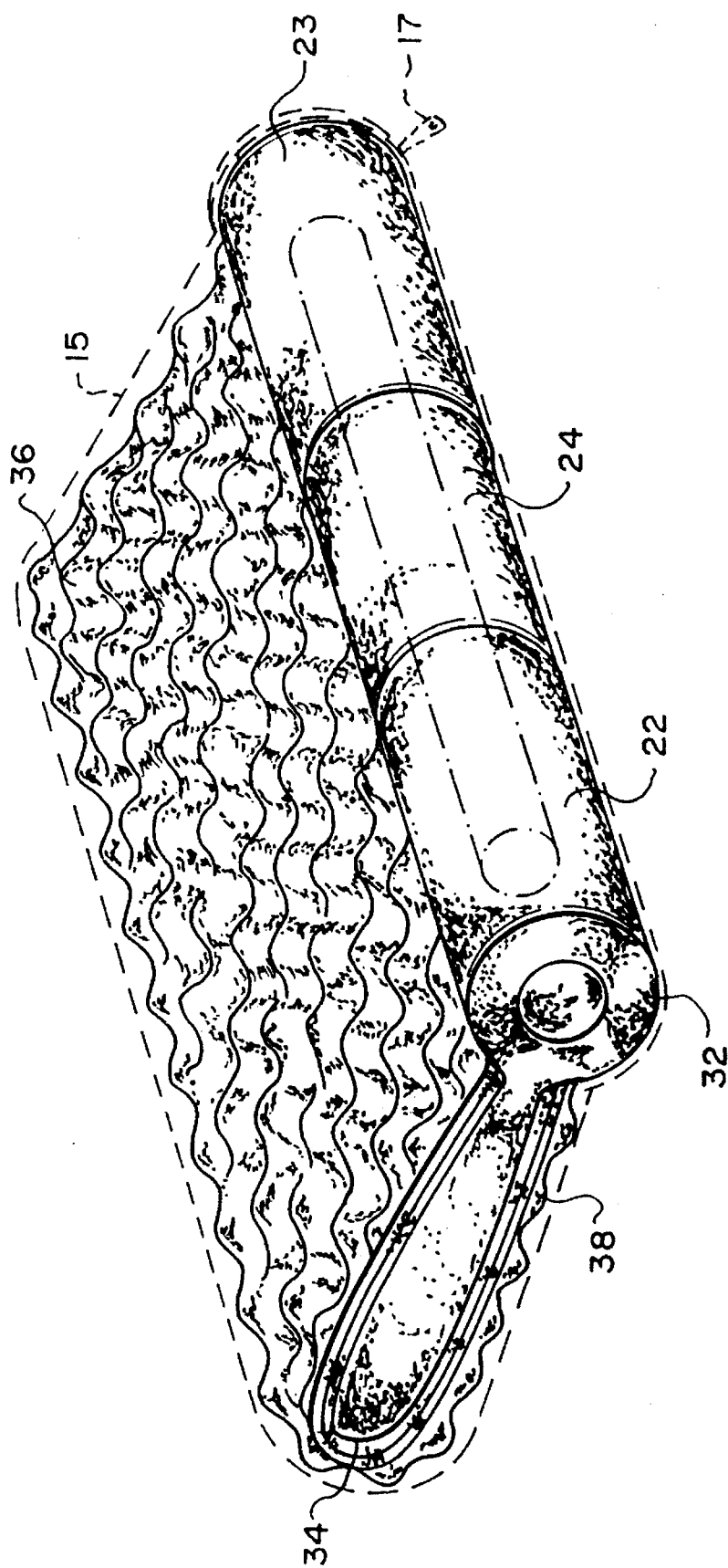
FIG. 2 is a perspective view of a combined cylindrical cervical roll and head cradle formed integrally from polyurethane foam.

In FIG. 2, there may be seen a pillow which combines a cervical roll of the type described and shown in FIG. 1, with a head cradle. The cervical roll and the head cradle are preferably formed integrally, and in one fabrication method, three blocks of polyurethane foam are laminated together in a sandwich. The outside blocks are each 8" in thickness and the center block is 6" in thickness, the total structural thickness being about 20". The triple laminated foam block may be placed on a contour saw table and cut to a keyhole shape as shown in the sectional end view at 32–34 in FIG. 2. As in the case of the cervical roll alone shown in FIG. 1, the center block 24 is preferably made of relatively soft foam which may have a density of about 1.4 and a firmness of about 12 lbs. Indent Load Deflection. The foam used in the end portions 22 and 23 may also average about 1.4 density, but has a firmness of about 20 lbs. Indent Load Deflection. The head cradle by reason of its being cut from the same three laminated blocks as the cervical roll also has a relatively soft central portion and relatively firm end portions as in the roll.

In fabricating the pillow, in addition to cutting the keyhole shape, the central core of the cervical roll is also removed, again in the same manner as the roll of FIG. 1. In the central opening of the cervical roll, a gel pack may be inserted. The gel pack is also the same as that of the embodiment of FIG. 1.

To provide additional comfort in the pillow, there may be laminated to the top and bottom surfaces of the head cradle layers of soft convoluted foam 36 and 38. The entire pillow, including the cervical roll and the head cradle, may be fitted with a polycotton cover indicated in phantom at 15 having zippered openings indicated in phantom at 17 in one or both ends of the cervical roll to permit the insertion and removal of the cylindrical gel pack.

In FIG. 3, there is shown a pillow which follows the design of FIG. 2 in that it includes a cervical roll and a head cradle. In the particular assembly of this pillow however, using polyester fiber, the cervical roll 40 and the head cradle 41 are fabricated separately. First, a length of 40" wide batting is folded in upon itself about 8" on each side, thereby reducing the width of the pillow from 40" to 24" overall. The polyester batting may have a length of about 22" and an additional sheet of polycotton material 22"×24" may be placed on top. The batting is then rolled and stitched to form a tubular core 40. The batting is preferably made from 1 ¼" staple fibers of 6 denier layered with resin to form a slickened polyester fiber. The head cradle 41 may be manufactured by utilizing the same slickened polyester fiber blown into a casing composed of polycotton material. For a pillow of the size of the embodiment described, about ¾ of a pound of polyester fiber is sufficient. The opening in the cervical roll formed by rolling the batting material is of the appropriate dimensions, namely about 2" in diameter, to accept a cylindrical gel pack of the type described hereinabove. The pillow may be enclosed in a polycotton cover indicated in phantom at 15 with suitable zippered openings indicated at 17 at one or both ends of the cervical roll to permit insertion and removal of the cylindrical gel pack.

The gel pack will provide effective hot therapy for a period of about a half-hour after it has been exposed to microwave radiation for two to two and one-half minutes. Cold therapy for about one half-hour is available after freezing the gel pack for about two hours.

What is claimed is:

1. A hot and cold therapeutic pillow comprising a cervical roll having a cylindrical container made of fabric and having a zippered opening formed in at least one end, a toroidal length of plastic material having two similar relatively firm end portions and a relatively soft central portion disposed in said cylindrical container, a cylindrical gel pack removably disposed within the axial opening of said toroidal length of plastic, said gel pack being capable of reaching and maintaining an elevated temperature upon being subjected to microwave radiation and capable of reaching and maintaining a reduced temperature upon being subjected to freezing.

2. A hot and cold therapeutic pillow comprising a cervical roll having end portions composed of relatively firm high density polyurethane foam and a central portion composed of relatively soft low density polyurethane foam, said cervical roll having a cylindrical axial opening formed therethrough, a cylindrical gel pack removably disposed in said axial opening, said gel pack being capable of reaching and maintaining an elevated temperature when subjected to microwave radiation and capable of reaching and maintaining a reduced temperature when subjected to freezing.

3. In a hot and cold therapeutic pillow as defined in claims 1, the combination in which said plastic material is composed of slickened polyester fibers.

4. A hot and cold therapeutic pillow as defined in claim 1 and further comprising a head cradle attached to the periphery of said cervical roll and extending outwardly therefrom, said head cradle also being made of plastic material and having two relatively firm end portions and a relatively soft central portion, the end portions of said head cradle being aligned with the end portions of said cervical roll and the central portion of said head cradle being aligned with the central portion of said cervical roll.

5. A hot and cold therapeutic pillow as defined in claim 4 wherein said plastic material is composed of polyurethane foam.

6. A hot and cold therapeutic pillow as defined in claim 4 wherein said plastic material is composed of slickened polyester fibers.

7. A hot and cold therapeutic pillow as defined in claim 6 and further including a layer of convoluted polyurethane foam laminated to each side of said head cradle.

\* \* \* \* \*